United States Patent
Tallinen et al.

(10) Patent No.: US 12,324,929 B2
(45) Date of Patent: Jun. 10, 2025

(54) TRAJECTORY OPTIMIZATION USING DOSE ESTIMATION AND CONFLICT DETECTION

(71) Applicant: SIEMENS HEALTHINEERS INTERNATIONAL AG, Steinhausen (CH)

(72) Inventors: Tuomas Tallinen, Espoo (FI); Daniel Valenzuela, Helsinki (FI); Janne Nord, Espoo (FI)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 87 days.

(21) Appl. No.: 17/973,426

(22) Filed: Oct. 25, 2022

(65) Prior Publication Data
US 2023/0057253 A1 Feb. 23, 2023

Related U.S. Application Data

(63) Continuation of application No. 17/036,176, filed on Sep. 29, 2020, now Pat. No. 11,478,661.

(51) Int. Cl.
*A61N 5/10* (2006.01)

(52) U.S. Cl.
CPC .......... *A61N 5/1031* (2013.01); *A61N 5/10* (2013.01); *A61N 5/103* (2013.01); *A61N 5/1042* (2013.01);
(Continued)

(58) Field of Classification Search
CPC ........ A61N 5/10; A61N 5/103; A61N 5/1031; A61N 5/1042; A61N 5/1045;
(Continued)

(56) References Cited

U.S. PATENT DOCUMENTS

| 6,546,073 B1 * | 4/2003 | Lee ................. A61N 5/1031 378/65 |
| 7,027,557 B2 * | 4/2006 | Llacer ............. A61N 5/1031 378/65 |

(Continued)

FOREIGN PATENT DOCUMENTS

| WO | WO-2018/222751 A1 | 12/2018 |
| WO | WO-2019/213743 A1 | 11/2019 |

OTHER PUBLICATIONS

International Search Report dated Jan. 21, 2022 and Written Opinion on PCT Appl. Serial No. PCT/EP2021/076173 (9 pages).

*Primary Examiner* — Allen C. Ho
(74) *Attorney, Agent, or Firm* — Foley & Lardner LLP

(57) ABSTRACT

Systems and methods for radiation treatment planning can include a computing system determining an estimate of a radiation dose distribution within an anatomical region of a patient, and determining a cost matrix representing an objective function, using the estimate of the radiation dose distribution. The computing system can project the cost matrix on each of a plurality of fluence planes. Each of the plurality of fluence planes can be associated with a corresponding gantry-couch orientation of a plurality of gantry-couch orientations of a medical linear accelerator. The computing system can determine, using projections of the cost matrix on each of the plurality of fluence planes, a sequence of gantry-couch orientations among the plurality of gantry-couch orientations representing a treatment path.

20 Claims, 6 Drawing Sheets

(52) U.S. Cl.
CPC ......... *A61N 5/1045* (2013.01); *A61N 5/1047* (2013.01); *A61N 5/1077* (2013.01); *A61N 5/1081* (2013.01)

(58) Field of Classification Search
CPC .. A61N 5/1047; A61N 5/1077; A61N 5/1081; A61N 5/1082
USPC .......................................................... 378/65
See application file for complete search history.

(56) References Cited

U.S. PATENT DOCUMENTS

| | | | | |
|---|---|---|---|---|
| 7,369,645 B2* | 5/2008 | Lane | .................... | A61N 5/1031 378/65 |
| 7,590,219 B2* | 9/2009 | Maurer, Jr. | ............ | G21K 1/046 378/65 |
| 7,876,882 B2* | 1/2011 | Meyer | .................... | A61N 5/103 378/65 |
| 7,906,770 B2* | 3/2011 | Otto | .................... | A61N 5/1047 378/65 |
| 8,262,554 B2* | 9/2012 | Sayeh | .................... | A61B 6/032 378/65 |
| 9,289,627 B2 | 3/2016 | Otto | | |
| 9,507,886 B2* | 11/2016 | Fiege | .................... | G06N 3/126 |
| 9,700,738 B2 | 7/2017 | Martin et al. | | |
| 9,849,306 B2 | 12/2017 | Kesti-Helia et al. | | |
| 10,080,911 B2* | 9/2018 | Zankowski | .......... | A61N 5/1031 |
| 10,279,196 B2* | 5/2019 | West | .................... | A61N 5/1031 |
| 10,307,615 B2* | 6/2019 | Ollila | .................... | A61N 5/1039 |
| 10,449,388 B2* | 10/2019 | Yin | ........................ | A61N 5/103 |
| 10,493,299 B2 | 12/2019 | Hissoiny | | |
| 10,507,337 B2 | 12/2019 | Willcut et al. | | |
| 10,549,116 B2* | 2/2020 | Sheng | .................. | A61N 5/1082 |
| 10,639,501 B2* | 5/2020 | Peltola | .................. | A61N 5/1081 |
| 10,668,300 B2 | 6/2020 | Hissoiny et al. | | |
| 10,668,304 B2 | 6/2020 | Magro et al. | | |
| 10,688,320 B2* | 6/2020 | Voronenko | .......... | A61N 5/1065 |
| 10,821,300 B2 | 11/2020 | Isola et al. | | |
| 10,850,121 B2* | 12/2020 | Moore | .................. | A61N 5/1031 |
| 10,967,200 B2 | 4/2021 | Stahl et al. | | |
| 11,027,148 B2 | 6/2021 | Bokrantz et al. | | |
| 11,065,471 B2* | 7/2021 | Wu | ........................ | A61N 5/103 |
| 11,077,320 B1 | 8/2021 | Hibbard | | |
| 11,097,128 B2 | 8/2021 | Sjolund | | |
| 11,100,632 B2 | 8/2021 | Han | | |
| 11,147,985 B2* | 10/2021 | Isola | .................... | A61N 5/1031 |
| 11,278,737 B2* | 3/2022 | Peltola | ................ | A61N 5/1031 |
| 11,291,858 B2 | 4/2022 | MacDonald et al. | | |
| 11,376,445 B1* | 7/2022 | Adamson | ............ | A61N 5/1031 |
| 11,400,313 B2* | 8/2022 | Ollila | .................... | A61N 5/1031 |
| 11,478,661 B2* | 10/2022 | Tallinen | ............... | A61N 5/1045 |
| 11,590,362 B2* | 2/2023 | Harju | .................. | A61N 5/1031 |
| 11,679,273 B2* | 6/2023 | Kauppinen | .......... | A61N 5/1031 600/1 |
| 11,826,560 B2* | 11/2023 | Zhang | .................. | A61N 5/1031 |
| 11,992,702 B2* | 5/2024 | Hibbard | ................ | A61N 5/1031 |
| 2008/0242969 A1 | 10/2008 | Sayeh et al. | | |

\* cited by examiner

TRAJECTORY OPTIMIZATION USING DOSE ESTIMATION AND CONFLICT DETECTION

CROSS-REFERENCE TO RELATED APPLICATIONS

This application is a continuation application of U.S. application Ser. No. 17/036,176, filed Sep. 29, 2020, now issued as U.S. Pat. No. 11,478,661, on Oct. 25, 2022, which is incorporated herein in its entirety for all purposes.

FIELD OF THE DISCLOSURE

The present application relates generally to systems and methods for automatic radiotherapy treatment planning. Specifically, the present application relates to automatic radiotherapy treatment planning using an estimated radiation dose distribution and detection of conflicts with respect to, for example, organs at risk (OARs).

BACKGROUND

Radiotherapy is a radiation-based therapy that is used as a cancer treatment. Specifically, high doses of radiation are used to kill or shrink a tumor. The target region of a patient's body that is intended to receive radiation (e.g., tumor) is referred to as the planning target volume (PTV). The goal is to deliver enough radiation to the PTV to kill the cancerous cells. However, other organs or anatomical regions that are adjacent to, or surrounding, the PTV can be in the way of radiation beams and can receive enough radiation to damage or harm such organs or anatomical regions. These organs or anatomical regions are referred to as organs at risk (OARs). Usually a physician or a radiologist identifies both the PTV and the OARs prior to radiotherapy using, for example, computed tomography (CT) images, magnetic resonance imaging (MRI) images, positron emission tomography (PET) images, images obtained via some other imaging modality, or a combination thereof. For instance, the physician or the radiologist may manually mark the PTV and/or the OARs on the medical images of the patient.

Using the medical images of the patient as well as the identified PTV and the OARs, a team of medical personnel (e.g., physicians, radiologists, oncologists, radiology technicians, other medical personnel or a combination thereof), referred to herein as the treatment planner, determines the radiation parameters to be used during the radiotherapy treatment. These radiation parameters include, for example, the type, the angle, the radiation intensity and/or the shape of each radiation beam. In determining these parameters, the treatment planner attempts to achieve a radiation dose distribution to be delivered to the patient that meets predefined criteria, e.g., set by the team. Such criteria usually include predefined radiation dose thresholds or ranges for the PTV and the OARs to be met.

To optimize the radiation parameters in a way to meet the predefined criteria, the treatment planner usually runs a plurality of simulations with various radiation parameters, and selects a final set of radiation parameters to be used based on the simulation results. This process usually involves tweaking the radiation parameters after each simulation. Such approach is time consuming, tedious and may not provide optimal results. For instance, a patient can wait for days or weeks before a radiation therapy plan specific to the patient is ready.

SUMMARY

Embodiments described herein relate to an automated trajectory planning approach for use in radiation treatment planning. Using medical images of the anatomy of a patient, a computing device can estimate an expected radiation dose distribution or a typical realizable dose distribution within an anatomical region of a patient's body. Given an objective function defined in terms of the estimated distribution and dosimetric goals for PTV and OARs, the computing device can compute a cost matrix representing the objective function defined in terms of the dose estimate, and project the cost matrix on available fluence planes. The computing device can use the projections of the cost matrix to detect conflicts with predefined medical goals (e.g., related to the amount of acceptable radiation dose in various organs of the patient), and identify a radiation trajectory based on the identified conflicts. For each possible orientation of the gantry and couch of a radiation machine, a corresponding value defined based on the corresponding projection of the cost matrix is used as a metric to determine whether the orientation belongs to the final radiation trajectory.

According to one aspect, a method of radiation treatment planning can include one or more processors determining an estimate of radiation dose distribution within an anatomical region of a patient. The method can include the one or more processors determining a cost matrix representing an objective function, using the estimate of radiation dose distribution. The objective function can be defined in terms of the estimate of radiation dose distribution and patient specific data. The method can include the one or more processors projecting the cost matrix on each of a plurality of fluence planes. Each of the plurality of fluence planes can be associated with a corresponding gantry-couch orientation of a plurality of gantry-couch orientations of a medical linear accelerator. The method can include the one or more processors determining, using projections of the cost matrix on each of the plurality of fluence planes, a sequence of gantry-couch orientations among the plurality of gantry-couch orientations representing a treatment path.

In some implementations, determining the estimate of radiation dose distribution can include determining the estimate of radiation dose distribution as a function of a distance from a planning target volume (PTV) of the anatomical region. The objective function can reflect one or more radiation constraints for the patient. The objective function can be defined to optimize an intensity modulated radiation therapy (IMRT) based radiation plan. The objective function can be defined to optimize a volumetric modulated arc therapy (VMAT) based radiation plan. The method can include determining the plurality of gantry-couch orientations by discretizing a space of possible gantry-couch orientations. Each point of a discretized space of possible gantry-couch orientations can represent a corresponding gantry-couch orientation of the plurality of gantry-couch orientations.

In some implementations, projecting the cost matrix on each of a plurality of fluence planes can include applying a weighted projection. Applying the weighted projection can include weighing projected values of the cost matrix according to a depth relative to a planning target volume (PTV) inside the anatomical region in a direction of a radiation beam. Determining the sequence of gantry-couch orientations can include computing, for each gantry-couch orientation, a corresponding matrix sum value representing a sum of a projection of the cost matrix on a target mask of a fluence plane associated with the gantry-couch orientation, and determining the sequence of gantry-couch orientations using matrix sum values computed for the plurality of gantry-couch orientations. Determining the sequence of gantry-couch orientations can include minimizing a total of matrix sum values over the treatment path. The treatment path can extend over a predefined range of gantry-couch orientations.

According to one other aspect, a radiation treatment planning system can include one or more processors and a memory to store computer code instructions. The computer code instructions, when executed, can cause the one or more processors to determine an estimate of radiation dose distribution within an anatomical region of a patient. The one or more processors can determine, using the estimate of radiation dose distribution, a cost matrix representing an objective function. The objective function can be defined in terms of the estimate of radiation dose distribution and patient specific data. The one or more processors can project the cost matrix on each of a plurality of fluence planes. Each of the plurality of fluence planes can be associated with a corresponding gantry-couch orientation of a plurality of gantry-couch orientations of a medical linear accelerator. The one or more processors can determine, using projections of the cost matrix on each of the plurality of fluence planes, a sequence of gantry-couch orientations among the plurality of gantry-couch orientations representing a treatment path.

In some implementations, determining the estimate of radiation dose distribution can include determining the estimate of radiation dose distribution as a function of a distance from a planning target volume (PTV) of the anatomical region. The objective function can reflect one or more radiation constraints for the patient. The objective function can be defined to optimize an intensity modulated radiation therapy (IMRT) based radiation plan or to optimize a volumetric modulated arc therapy (VMAT) based radiation plan. The one or more processors can further determine the plurality of gantry-couch orientations by discretizing a space of possible gantry-couch orientations. Each point of a discretized space of possible gantry-couch orientations can represent a corresponding gantry-couch orientation of the plurality of gantry-couch orientations.

In some implementations, in projecting the cost matrix on each of a plurality of fluence planes, the one or more processors can apply a weighted projection. In applying the weighted projection, the one or more processors can weigh projected values of the cost matrix according to a depth relative to a planning target volume (PTV) in a direction of a radiation beam inside the anatomical region. In determining the sequence of gantry-couch orientations, the one or more processors can (i) compute, for each gantry-couch orientation, a corresponding matrix sum value representing a sum of a projection of the cost matrix on a target mask of a fluence plane associated with the gantry-couch orientation, and (ii) determine the sequence of gantry-couch orientations using matrix sum values computed for the plurality of gantry-couch orientations. In determining the sequence of gantry-couch orientations, the one or more processors can minimize a total of matrix sum values over the treatment path. The treatment path can extend over a predefined range of gantry-couch orientations.

According to yet one other aspect, a computer readable medium can include computer code instructions stored thereon. The computer code instructions when executed can cause one or more processors to determine an estimate of radiation dose distribution within an anatomical region of a patient, and determine, using the estimate of radiation dose distribution, a cost matrix representing an objective function defined in terms of the estimate of radiation dose distribution and patient specific data. Execution of the computer code instructions can cause the one or more processors to project the cost matrix on each of a plurality of fluence planes. Each of the plurality of fluence planes can be associated with a corresponding gantry-couch orientation of a plurality of gantry-couch orientations of a medical linear accelerator. The one or more processors can determine, using projections of the cost matrix on a target mask of each of the plurality of fluence planes, a sequence of gantry-couch orientations among the plurality of gantry-couch orientations representing a treatment path.

Figure 1A:
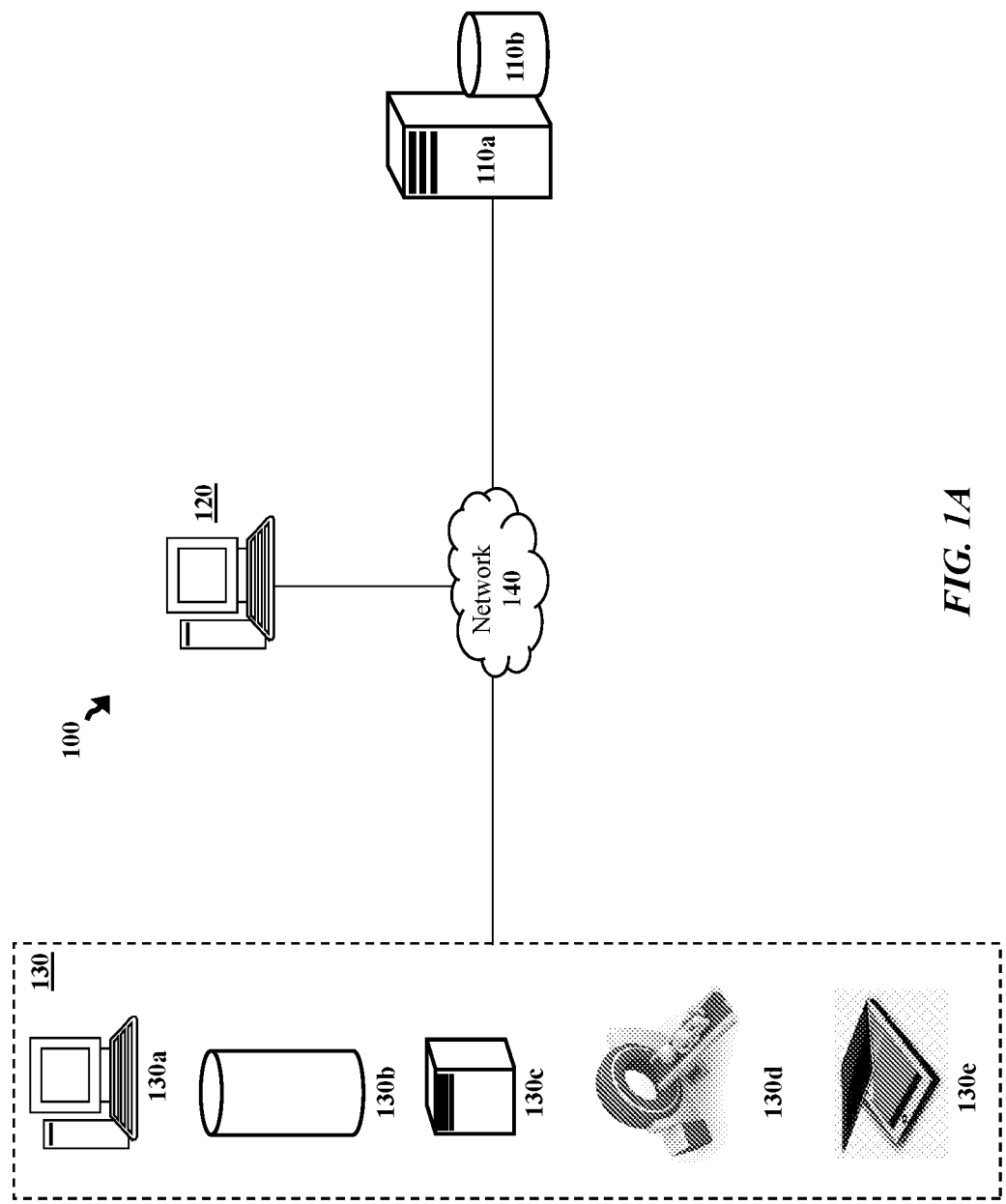
FIG. 1A shows a block diagram illustrating an example computer environment for implementing methods and processes described herein, according to an embodiment.

Some or all of the figures are schematic representations for purposes of illustration. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

DETAILED DESCRIPTION

Following below are more detailed descriptions of various concepts related to, and implementations of, methods, apparatuses, and systems for radiation treatment planning. The various concepts introduced above and discussed in greater detail below may be implemented in any of numerous ways as the described concepts are not limited to any particular manner of implementation. Examples of specific implementations and applications are provided primarily for illustrative purposes.

Radiotherapy treatment planning is a complex and patient specific optimization problem. Given the anatomy of the patient, e.g., as illustrated in medical images of the patient, and identifications or masks of the PTV and the OARs, the goal is to determine a treatment path (or treatment trajectory) that satisfies the criteria or constraints predefined, for example, by physicians, radiologists or other medical personnel. During radiotherapy sessions, the patient usually lies down on the couch of a radiation machine, and a gantry equipped with a radiation source rotates around the patient to deliver radiation from different angles with various intensities and/or shapes. Determining the treatment path or trajectory includes determining a sequence of positions of the radiation source (e.g., relative to the patient) and corresponding radiation angles (e.g., in the 3-D space) defining the positions and orientations of the radiation source at which radiation beams are emitted towards the patient. The sequence of positions of the radiation source defines a rotation path or trajectory of the gantry around the patient. Determining the radiation path can also include determining, for each radiation position and angle of the sequence of radiation positions and angles, a corresponding radiation intensity and/or beam shape.

Optimization of the radiation treatment trajectory or path leads to improvement of dosimetric quality of a treatment plan. Specifically, the goal of the optimization is to minimize (or maintain below a corresponding predefined upper bound value) the amount of radiation dose for OARs while maximizing (or maintain above a corresponding predefined lower bound value) the radiation dose for the PTV. In such a case, the radiotherapy designed according to the optimized radiation treatment trajectory can lead to killing the cancerous cells without damaging or harming critical organs or OARs. Trajectory optimization methods based on manual selection and prioritization of critical organs make the task of treatment planners difficult, are time consuming for users, requires a trial and error procedure, and the outcome usually depends on the experience and skill of the treatment planner.

In the current disclosure, systems and methods for improved automatic radiation treatment planning start with an estimate of expected radiation dose distribution within an anatomical region of the patient's body, and identify conflicts between the estimate of the radiation dose distribution and clinical goals for the plan. The systems and methods described herein can determine or optimize the treatment trajectory or path by taking into account spatial regions where conflicts are expected. The severity of the conflicts can be expressed via an objective (or cost) function that can be evaluated at each voxel of the 3-D anatomical region. The systems and methods described herein can generate a radiation treatment trajectory or path that avoids conflicts based on their severity, for example, as expressed or described in the cost function.

Embodiments described herein allow for automated trajectory planning. As such, there's no need for a user to select or adjust weights for critical organs in generating gantry-couch direction quality-landscapes to be used for treatment path finding. Also, the embodiments described herein provide finer spatial precision (e.g., more accurate than per structure) as weighting of the 3-D patient at various steps of the methods described herein can be applied at the voxel level. For instance, in some cases, clinical goals may call for avoiding only a specific region of a critical organ instead of avoiding the whole organ. The finer spatial precision leads to improved final treatment trajectories with respect to the patient specific clinical goals or dose volume objectives.

FIG. 1A illustrates an example computer environment 100 that can be used to provide a network-based implementation of the methods described herein. The computer environment 100 can include a computer server 110a, system database 110b, a user computing device 120 and electronic data sources 130a-e (collectively electronic data source 130). The above-mentioned components may be connected to each other through a network 140. The examples of the network 140 may include, but are not limited to, private or public LAN, WLAN, MAN, WAN, and the Internet. The network 140 may include both wired and wireless communications according to one or more standards and/or via one or more transport mediums.

The communication over the network 140 may be performed in accordance with various communication protocols such as Transmission Control Protocol and Internet Protocol (TCP/IP), User Datagram Protocol (UDP), and IEEE communication protocols. In one example, the network 140 may include wireless communications according to Bluetooth specification sets or another standard or proprietary wireless communication protocol. In another example, the network 140 may also include communications over a cellular network, including, e.g., a GSM (Global System for Mobile Communications), CDMA (Code Division Multiple Access), EDGE (Enhanced Data for Global Evolution) network.

The computer environment 100 is not necessarily confined to the components described herein and may include additional or alternate components, not shown for brevity, which are to be considered within the scope of the embodiments described herein.

In some implementations, the computer server 110a can be configured to execute computer instructions to perform any of the methods described herein or operations thereof. The computer server 110a may generate and display an electronic platform to display information indicative of, or related to, a radiation plan trajectory. The electronic platform may include graphical user interface (GUI) displayed on the user computing device 120. An example of the electronic platform generated and hosted by the computer server 110a may be a web-based application or a website configured to be displayed on different electronic devices, such as mobile devices, tablets, personal computer, and the like (e.g., user computing device 120).

The computer server 110a may host a website accessible to end-users, where the content presented via the various webpages may be controlled based upon each particular user's role or viewing permissions. The computer server 110a may be any computing device comprising a processor and non-transitory machine-readable storage capable of executing the various tasks and processes described herein. Non-limiting examples of such computing devices may include workstation computers, laptop computers, server computers, laptop computers, and the like. While the computer environment 100 includes a single computer server 110a, in some configurations, the computer server 110a may include any number of computing devices operating in a distributed computing environment.

The computer server 110a may execute software applications configured to display the electronic platform (e.g., host a website), which may generate and serve various webpages to each user computing device 120. Different users operating the user computing device(s) 120 may use the website to view and/or interact with the output treatment trajectories or paths.

In some implementations, the computer server 110a may be configured to require user authentication based upon a set of user authorization credentials (e.g., username, password, biometrics, cryptographic certificate, and the like). In such implementations, the computer server 110a may access the system database 110b configured to store user credentials, which the computer server 110a may be configured to reference in order to determine whether a set of entered credentials (purportedly authenticating the user) match an appropriate set of credentials that identify and authenticate the user.

In some configurations, the computer server 110a may generate and host webpages based upon a particular user's role (e.g., administrator, employee, and/or bidder). In such implementations, the user's role may be defined by data fields and input fields in user records stored in the system database 110b. The computer server 110a may authenticate the user and may identify the user's role by executing an access directory protocol (e.g. LDAP). The computer server 110a may generate webpage content that is customized according to the user's role defined by the user record in the system database 110b.

In some embodiments, the computer server 110a receives medical images, masks and/or medical data indicative of medical goals from a user (or retrieve from a data repository), process the data, and displays an indication of the treatment trajectory on the electronic platform. For instance, in a non-limiting example, a user operating the computing device 130a uploads a series of images of a CT scan or other medical images using the electronic platform. The computer server 110a can determine the treatment trajectory based on input data, and display the results via the electronic platform on the user computing device 120 or the computing device 130a. The user computing device 120 and/or the computing device 130a may be any computing device comprising a processor and a non-transitory machine-readable storage medium capable of performing the various tasks and processes described herein. Non-limiting examples of a network node may be a workstation computer, laptop computer, tablet computer, and server computer. In operation, various users may use user computing devices 120 and or computing device 130a to access the GUI operationally managed by the computer server 110a.

The electronic data sources 130 may represent various electronic data sources that contain and/or retrieve medical images of patients. For instance, database 130b and third-party server 130c may represent data sources providing the corpus of data (e.g., medical images, masks or other medical data) needed for the computer server 110a to determine treatment trajectories. The computer server 110a may also retrieve the data directly from a medical scanner 130e and/or medical imaging device 130d (e.g., CT scan machine).

In some implementations, the methods described herein or operations thereof can be implemented by the user device 120, any of the electronic devices 130 or a combination thereof.

While FIG. 1A shows a network based implementation, it is to be noted that methods described herein can be implemented by a single computing device that receives the medical images and medical data for a patient and determines a radiation treatment trajectory or path according to methods described herein.

Figure 1B:
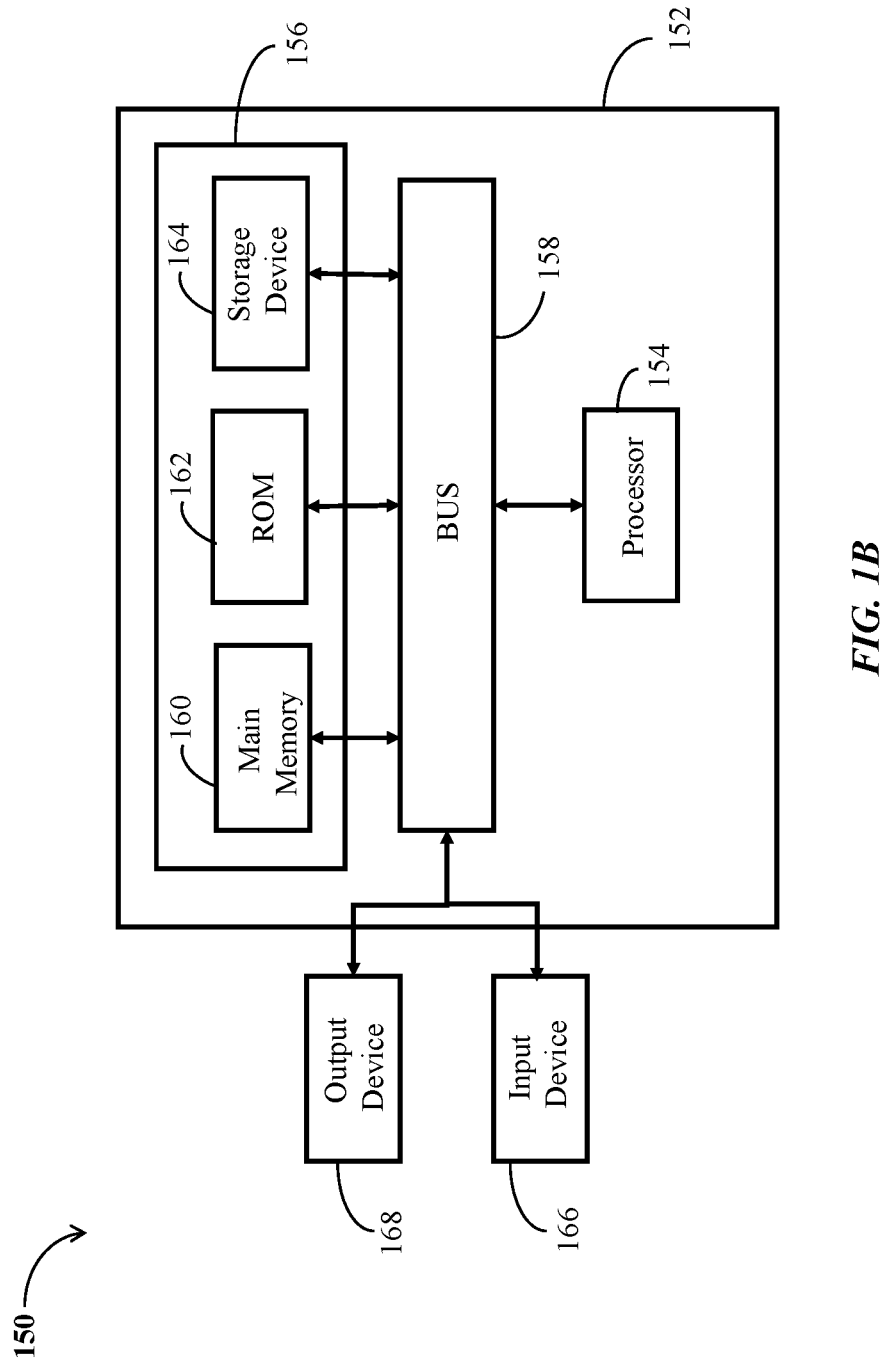
FIG. 1B is a block diagram depicting one implementation of a system architecture, according to an embodiment.

Referring to FIG. 1B, a block diagram depicting one implementation of a system architecture for a computing system 150 that may be employed to implement methods described herein is shown, according to inventive concepts of the current disclosure. The computing system 150 can include a computing device 152. The computing device 152 can represent an example implementation of any of the devices 110a, 120 and/or 130a-e of FIG. 1A. For instance, the computing device 152 can include, but is not limited to, a computed tomography (CT) scanner, a medical linear accelerator device, a desktop, a laptop, a hardware computer server, a workstation, a personal digital assistant, a mobile computing device, a smart phone, a tablet, or other type of computing device. The computing device 152 can include a one or more processors 154 to execute computer code instructions, a memory 156 and a bus 158 communicatively coupling the processor 154 and the memory 156.

The one or more processors 154 can include a microprocessor, a general purpose processor, a multi-core processor, a digital signal processor (DSP) or a field programmable gate array (FPGA), an application-specific integrated circuit (ASIC) or other type of processor. The one or more processors 154 can be communicatively coupled to the bus 158 for processing information. The memory 156 can include a main memory device 160, such as a random-access memory (RAM) other dynamic storage device, coupled to the bus 158 for storing information and instructions to be executed by the processor 154. The main memory device 160 can be used for storing temporary variables or other intermediate information during execution of instructions (e.g., related to methods described herein such as method 200) by the processor 154. The computing device 152 can include a read-only memory (ROM) 162 or other static storage device coupled to the bus 158 for storing static information and instructions for the processor 154. For instance, the ROM 162 can store medical images of patients, for example, received as input. The ROM 162 can store computer code instructions related to, or representing an implementation of, methods described herein. A storage device 164, such as a solid state device, magnetic disk or optical disk, can be coupled to the bus 158 for storing (or providing as input) information and/or instructions.

The computing device 152 can be communicatively coupled to, or can include, an input device 166 and/or an output device 168. The computing device 102 can be coupled via the bus 158 to the output device 168. The output device 168 can include a display device, such as a Liquid Crystal Display (LCD), Thin-Film-Transistor LCD (TFT), an Organic Light Emitting Diode (OLED) display, LED display, Electronic Paper display, Plasma Display Panel (PDP), or other display, etc., for displaying information to a user. The output device 168 can include a communication interface for communicating information to other external devices. An input device 166, such as a keyboard including alphanumeric and other keys, may be coupled to the bus 158 for communicating information and command selections to the processor 154. In another implementation, the input device 166 may be integrated within a display device, such as in a touch screen display. The input device 166 can include a cursor control, such as a mouse, a trackball, or cursor direction keys, for communicating direction information and command selections to the processor 154 and for controlling cursor movement on the display device.

According to various implementations, the methods described herein or respective operations can be implemented as an arrangement of computer code instructions that are executed by the processor(s) 154 of the computing system 150. The arrangement of computer code instructions can be read into main memory device 160 from another computer-readable medium, such as the ROM 162 or the storage device 164. Execution of the arrangement of computer code instructions stored in main memory device 160 can cause the computing system 150 to perform the methods described herein or operations thereof. In some implementations, one or more processors 154 in a multi-processor arrangement may be employed to execute the computer code instructions representing an implementation of methods or processes described herein. In some other implementations, hard-wired circuitry may be used in place of or in combination with software instructions to effect illustrative implementation of the methods described herein or operations thereof. In general, implementations are not limited to any specific combination of hardware circuitry and software. The functional operations described in this specification can be implemented in other types of digital electronic circuitry, in computer software, firmware, hardware or a combination thereof.

Figure 2:
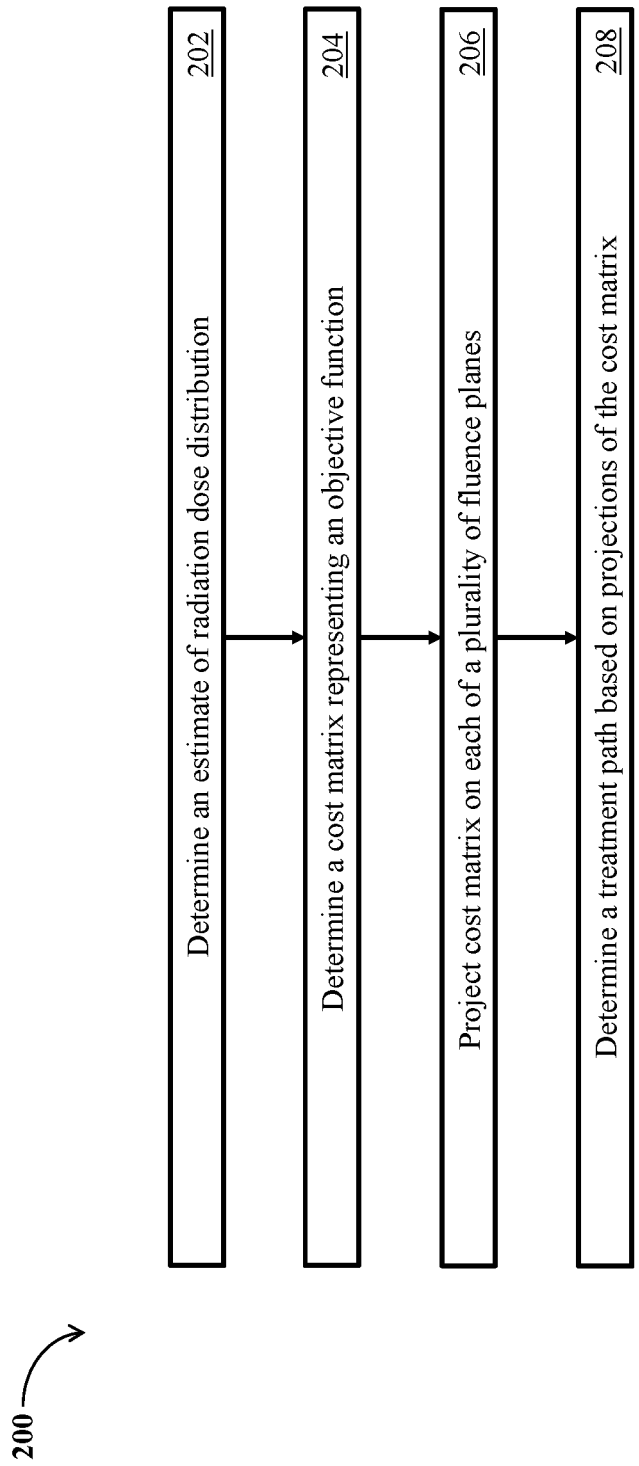
FIG. 2 is a flowchart illustrating an embodiment of a method of radiation treatment planning, according to an embodiment.

FIG. 2 shows a flowchart illustrating an embodiment of a method 200 of radiation treatment planning, according to inventive concepts of this disclosure. The method 200 can include the computing system 150 or device determining an estimate of radiation dose distribution within a patient's body (STEP 202), and determining a cost matrix representing an objective function (STEP 204). The method 200 can include the computing system 150 or computing device 152 projecting the cost matrix on each of a plurality of fluence planes or corresponding masks (STEP 206), and determining a treatment path based on projections of the cost matrix on the plurality of fluence planes or corresponding masks (STEP 208).

Referring back to FIGS. 1B and 2, the method 200 can include the computing system 150 or computing device 152 determining an estimate of radiation dose distribution within a patient's body (STEP 202). The computing system 150 can obtain medical images of an anatomy region of a patient, one or more structure masks of the PTV and OARs, information indicative of clinical goals, or a combination thereof. A CT scanner, an MM device, an ultrasound imaging device, a medical imaging device of other type or a combination thereof can generate the medical images of the patient. The medical images can include 3-D images, 2-D images or a combination thereof. Obtaining the one or more masks can include receiving the masks from another computing device. In some other implementations, the computing system 150 can segment one or more medical images of the patient, and generate the mask(s) using the segmented images. A user can tag segmented regions of the medical images as corresponding to the PTV or OARs. The information indicative of clinical goals can include, for each of the PTV and OARs, a corresponding radiation dose threshold, corresponding radiation dose range or corresponding desired radiation dose value. In some implementations, the radiation dose thresholds, ranges or desired values can be defined in connection with the one or more structure masks. The computing system 150 can receive the information indicative of clinical goals as input via the input device 166.

The estimate of radiation dose distribution can represent an expected radiation dose distribution, or a typical realizable dose distribution, within the anatomical region of the patient's body, responsive to the radiotherapy to be performed. The dose distribution estimate does not necessarily have to be the optimal radiation dose distribution. In some implementation, the computing system 150 or the processor 154 can generate the estimate of the radiation dose distribution as a function of distance from the PTV to model the usual falloff of the radiation dose around the PTV. The estimation can be isotropic to all directions from the PTV. In some implementations, the computing system 200 can generate the estimate of the radiation dose distribution as:

$$D(x) = \alpha \frac{d_0}{d(x) + d_0}, \quad (1)$$

where $d_0$ is constant and d represents a distance from the surface of the PTV. The variable x represents a point or voxel in the 3-D space, and a represents a coefficient that can be equal to, or defined relative to, the prescribed dose of the PTV. The computing system 150 can generate the estimate of the radiation dose distribution using some other function defined in terms of the distance d(x).

Figure 3C:
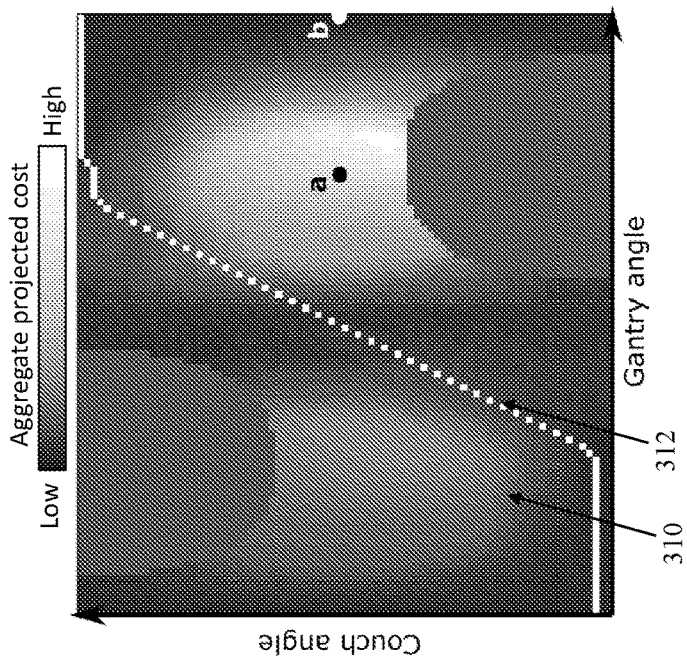
FIGS. 3A-3C show simulation results associated with various steps of the method of FIG. 2, according to an embodiment.
Figure 3B:
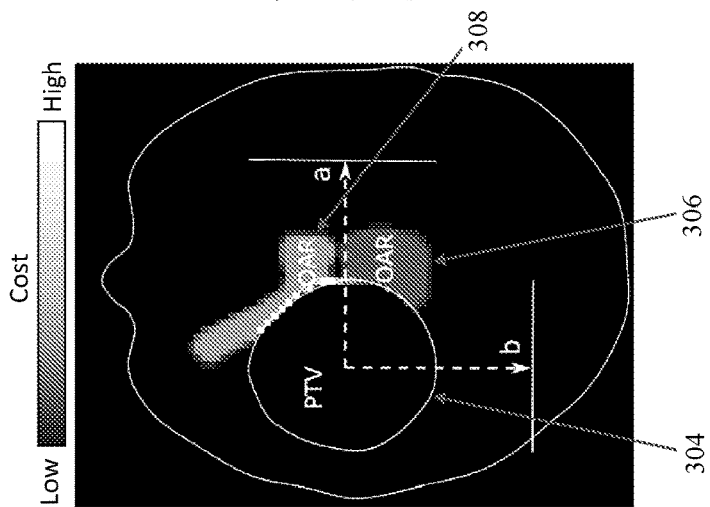
Figure 3A:
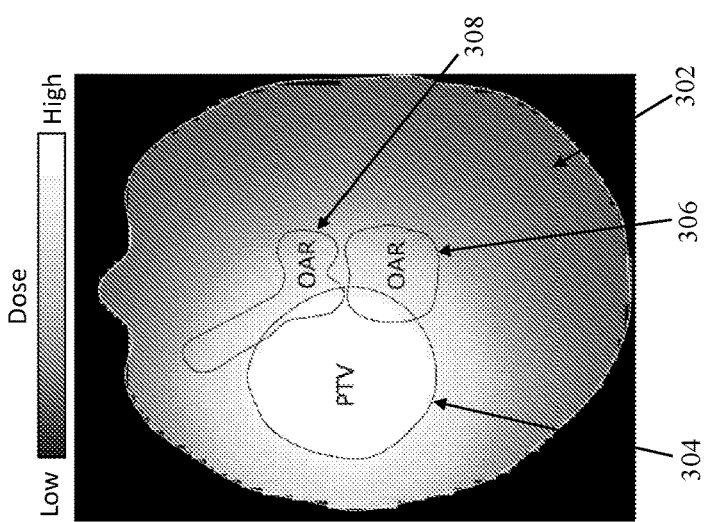

Referring to FIG. 3A, a 2-D slice of an example estimate of the radiation dose distribution with an anatomical region 302 is shown. The anatomical region 302 includes the PTV 304 and two OARs 306 and 308. The estimate of the radiation dose distribution shown in FIG. 3A is defined as D(x), as in equation (1). As illustrated in FIG. 3A, the radiation dose function D(x) decreases significantly outside the PTV 304.

In the case where the PTV includes a plurality of disjoint regions (e.g., a plurality of tumors or anomalies), the computing system 150 can generate or define the estimate of the radiation dose distribution in terms of the distance to each of the various PTV regions. For instance, at each voxel x, the computing system 150 can evaluate the expression $$\alpha \frac{d_0}{d(x) + d_0}$$

(or some other function of distance) for various distances to different PTV regions and use the maximum value as the radiation dose D(x) if the voxel x is outside any PTV region. If the voxel x is inside a PTV region, the computing system 150 or processor 154 can use the maximum value of the evaluated function of distance as the radiation dose D(x).

Referring back to FIGS. 1B and 2, the method 200 can include the computing system 150 or processor(s) 154 determining a cost matrix representing an objective function (STEP 204). The objective function can be defined in terms of the estimate of radiation dose distribution D(x) and patient specific data, such as dosimetric goals for PTV and OARs. In some implementations, the computing system 150 or processor(s) 154 can define the objective function as:

$$\Phi(x) = W(x)(D(x) - C(x))^2. \quad (2)$$

The objective function $\Phi(x)$ is defined at each voxel x as the square difference between the estimated radiation dose D(x) and a desired or reference radiation dose C(x) multiplied by a weighting value W(x). The reference radiation dose function C(x) can be defined, within each structure (e.g., PTV or OAR) of the anatomical region, to be equal to a corresponding constant dose value or threshold. The function C(x) can reflect dosimetric goals for PTV and OARs specific to the patient. For instance the function C(x) can be equal to a first radiation dose value within the PTV 304, equal to a second radiation dose value within the OAR 306, and equal to a third radiation dose value within the OAR 308. The first, second and third radiation dose values can be defined based on clinical or dosimetric goals specific to the patient. The weighting function W can reflect the severity of deviating from the radiation function C(x). In OARs, $\Phi(x)$ can be defined to be zero where $D(x) < C(x)$. The computing system 150 or processor(s) 154 can determine the value of voxel x of the cost matrix as $\Phi(x)$. Referring to FIG. 3B, a 2-D slice of an example cost matrix is shown. The cost matrix voxel values, or the corresponding objective function values, are calculated based on the objective function and estimated radiation dose distribution D(x) of FIG. 3A.

In some implementations, the cost matrix can be defined to represent the derivative $\partial_D \Phi$ of the objective function $\Phi(x)$ with respect to the radiation dose, or represent the absolute value of the derivative $\partial_D \Phi$. The computing system 150 or processor(s) 154 can define or compute the voxel value, at each voxel x of cost matrix, as the derivative $\partial_{D(x)} \Phi(x)$ of the objective function $\Phi(x)$ with respect to the radiation dose, or the corresponding absolute value $|\partial_{D(x)} \Phi(x)|$. In some implementations, the cost matrix can be defined differently. For instance, the computing system 150 or processor(s) 154 can define or compute the cost matrix as another function, e.g., other than the absolute value of the derivative, of the objective function $\Phi(x)$.

The method 200 can include the computing system 150 or processor(s) 154 projecting the cost matrix on each of a plurality of fluence planes (STEP 206). The computing system 150 or the processor(s) 154 can discretize a space of possible gantry-couch orientations. Each point of the discretized space of possible gantry-couch orientations can represent a corresponding gantry-couch orientation, e.g., (gantry angle, couch angle) pair, of the plurality of gantry-couch orientations. For instance, the space of possible gantry-couch orientations can be a 2-D space with the x-axis representing available gantry angles and the y-axis representing available couch angles or vice versa. That is, assuming that both the gantry and the couch are capable of moving or rotating, each relative orientation or position of the gantry and the couch can be expressed in terms of a corresponding gantry angle and a corresponding couch angle. Each of the gantry angle and couch angle can be defined in the 3-D space relative to corresponding reference directions. Each (gantry angle, couch angle) pair can define a corresponding position and/or orientation of the couch or the patient, and a corresponding position and/or orientation of the gantry or a corresponding direction of the radiated beam.

For each (gantry angle, couch angle) pair, the computing system 150 or processor(s) 154 can compute a projection of the cost matrix on a corresponding fluence plane. The computing system 150 or processor(s) 154 can project the voxels of the cost matrix along the corresponding radiation beam direction on the corresponding fluence plane. A voxel of a cost matrix is projected by determining the pixel at the fluence plane that is intersected by a ray that goes through the voxel in the direction of the radiation beam. The cost value of the voxel is added to the pixel value at the fluence plane.

In some implementations, the computing system 150 or the processor(s) 154 can apply a weighting to each of the projections of the cost matrix. For each projection of the cost matrix, the computing system 150 or the processor(s) 104 can apply corresponding weighted function defined in terms of a depth relative to a planning target volume (PTV) inside the anatomical region in a direction of a radiation beam. Applying the weighted projection can include weighing projected values of the cost matrix according to a depth relative to a planning target volume (PTV) inside the anatomical region in a direction of a radiation beam. The weight of projection from inside PTV can be assumed zero in order to include cost contributions only from OARs in the projections. For instance, the computing system 150 or the processor(s) 154 can apply higher weights to the volume before the PTV (considering the direction of the corresponding radiation beam) than the volume behind or after the PTV. Weight of PTV can be assumed to be equal to zero in order to include cost contributions only from OARs, or from all normal tissue including OARs, in the projections.

The method 200 can include the computing system 150 or the processor(s) 154 determining a treatment path based on projections of the cost matrix on the target masks of the plurality of fluence planes (STEP 208). The computing system 150 or the processor(s) 154 can compute for each (gantry angle, couch angle) pair a corresponding aggregate projection value representing the sum of the entries of the corresponding projection matrix. That is, for each (gantry angle, couch angle) pair, the computing system 150 or the processor(s) 154 can compute the sum of entries of the corresponding projection of the cost matrix to determine the corresponding aggregate projection value. In some implementations, a sum of entries is computed over a target mask of a fluence plane. A target mask can be formed by projecting voxels of a PTV to the fluence plane. The pixels receiving any projection are included in the target mask. Some margin around the target projection may be included in the mask. That is, projection of the cost matrix can be on the whole fluence plane, but only the part of the projection that hits the target mask is relevant for determining aggregate sums and thus a treatment path. The aggregate projection values corresponding to the (gantry angle, couch angle) pairs represent a measure of the severity of conflicts with the medical or clinical criteria or constraints. For a given (gantry angle, couch angle) pair, the corresponding aggregate projection value is indicative of whether a beam radiated by the gantry at the gantry angle and while the couch is oriented according to the couch angle violates any of the clinical or medical criteria set by the medical staff taking care of the patient. The larger the aggregate projection value, the more severe is the conflict associated with the corresponding (gantry angle, couch angle) pair.

The computing system 150 or the processor(s) 154 can use the computed aggregate projection values to determine the optimal treatment path or trajectory. Specifically, the computing system 150 or the processor(s) 154 can apply a path or trajectory search to a matrix of aggregate projection values to determine the optimal treatment path or trajectory. The columns of the matrix of aggregate projection values can correspond to different gantry angles and the rows can correspond to different couch angles, or vice versa. In performing the path search, the computing system 150 or the processor(s) 154 can start from an initial entry of the matrix of aggregate projection values and proceed iteratively to determine a sequence of entries until reaching a final entry. The computing system 150 or the processor(s) 154 can apply the path search in a way to minimize the corresponding total severity or the corresponding sum of aggregate projection values. For instance, the computing system 150 or the processor(s) 154 can apply a path search algorithm, such as the A*algorithm, to determine the path or trajectory having the smallest sum of aggregate projection values.

Each entry of the sequence of determined entries of the matrix of aggregate projection values represents a corresponding (gantry angle, couch angle) pair. As such, determining a sequence of entries of the matrix of aggregate projection values implies determining a sequence of (gantry angle, couch angle) pairs that form or represent the treatment path or trajectory. The input to the path search algorithm can include a starting point and an end point of the path. In some implementations, the starting point and the end point can be the same so that the path or trajectory forms a full loop around the patient. The computing system 150 or the processor(s) 154 can select the starting point as the (gantry angle, couch angle) pair corresponding to the smallest entry of the matrix of aggregate projection values. In some implementations, the computing system 150 or the processor(s) 154 can select the starting point differently.

Referring to FIG. 3C, an image of an example matrix of aggregate projection values 310 representing the severity of conflicts associated with possible (gantry angle, couch angle) pairs is shown together with a treatment path 312 that is determined based on the matrix of aggregate projection values 310. The treatment path 312 represents a sequence of (gantry angle, couch angle) pairs that define a loop around the patient. The gantry angles are equally spaced. The treatment path shown is associated with the minimum sum of corresponding entries of the matrix of aggregate projection values 310. The flat gray regions are forbidden either by those (gantry angle, couch angle) directions causing a collision or by the beam entering to the patient volume through clipping planes of the CT image. Points a and b in the aggregate projection matrix correspond to the projection directions a and b in FIG. 3B, respectively.

Figure 4B:
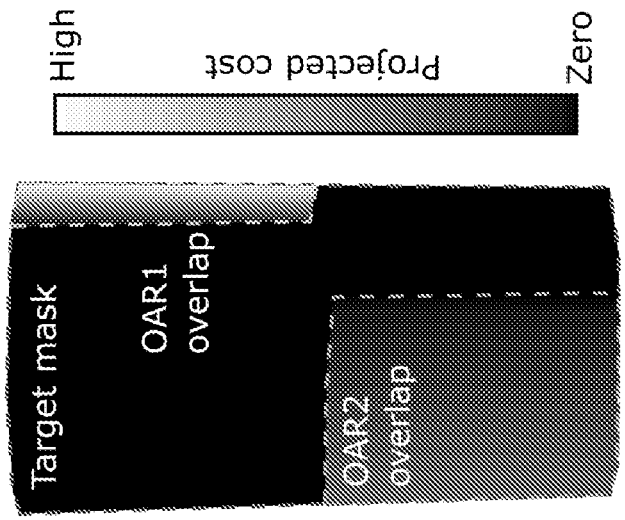
FIGS. 4A and 4B show images depicting a visual illustration of a projection of a cost matrix, according to an embodiment.
Figure 4A:
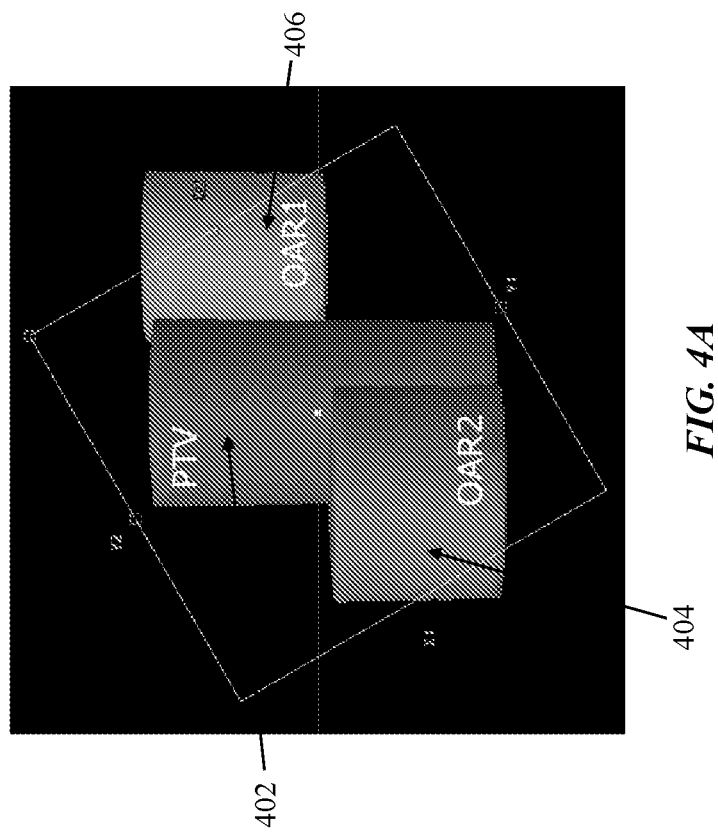

FIG. 4A shows an image depicting an example arrangement of various hypothetical anatomical structures. Structure 402 represents a PTV, while structures 404 and 406 represent two distinct OARs. FIG. 4B shows an image depicting a visual illustration of a projection of a cost matrix at the beam orientation corresponding to FIG. 4A. In this case, the OAR structure 406 is assumed to have clinical goals that are highly conflicting with the estimated radiation dose, therefore, producing high intensities in the projection of the cost matrix of FIG. 4B. In contrast, the OAR structure 404 is assumed to have clinical goals that are less conflicting with the estimated radiation dose, therefore, producing relatively low intensities in the projection of the cost matrix of FIG. 4B.

Figure 5B:
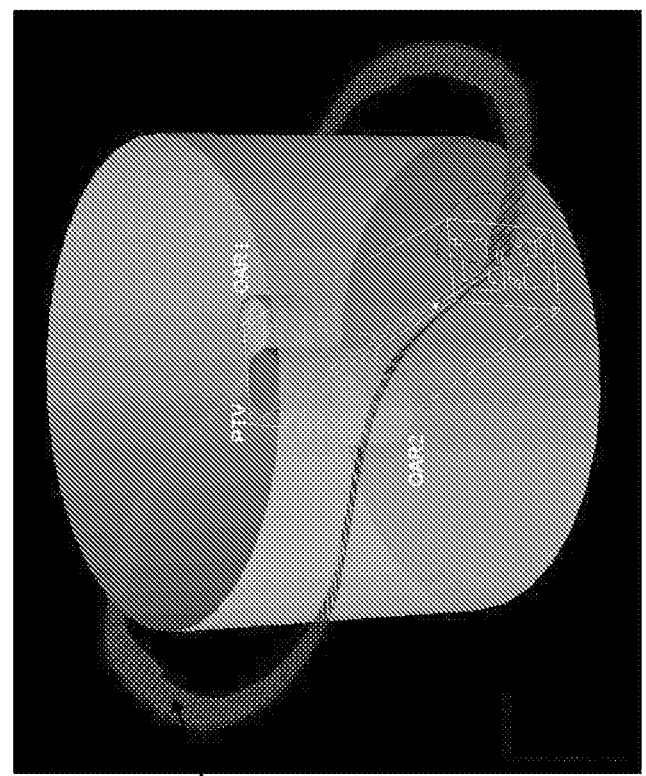
FIGS. 5A and 5B show images illustrating two-dimensional (2-D) and three-dimensional (3-D) representations of a treatment path, according to an embodiment.
Figure 5A:
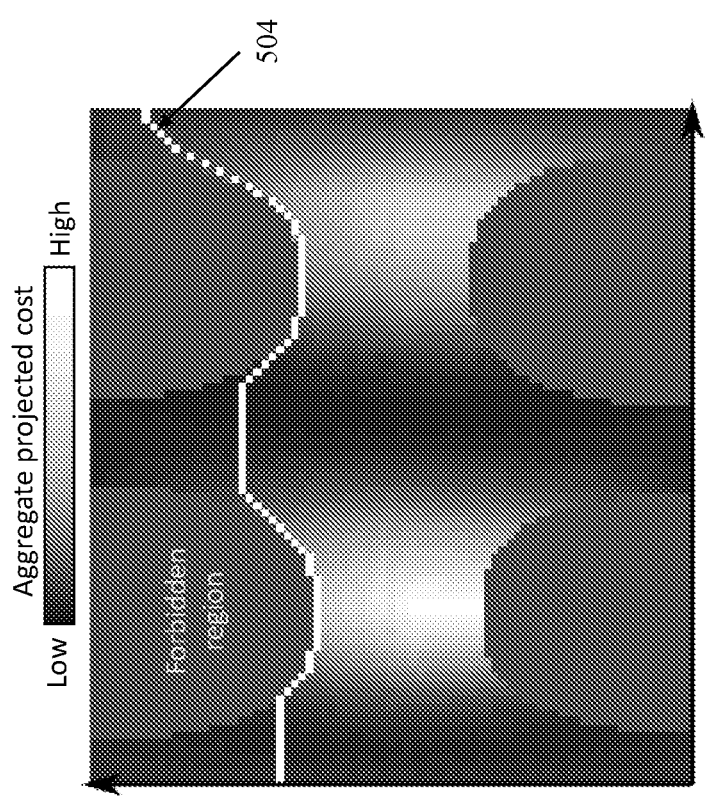

FIGS. 5A and 5B show images illustrating two-dimensional (2-D) and three-dimensional (3-D) representations of a treatment path, according to inventive concepts of this disclosure. FIG. 5A shows another example of a matrix of aggregate projection values and an optimal path 504 that minimizes the sum of corresponding entries of the aggregate projection matrix. The flat gray regions are forbidden either by those (gantry angle, couch angle) directions causing a collision or by the beam entering to the patient volume through clipping planes of the CT image. FIG. 5B shows the optimal path 502 in the 3-D space. FIG. 5B also illustrates a radiation beam at one point of the optimal path.

The computing system 150 or the processor(s) 154 can employ the method 200 to optimize an intensity modulated radiation therapy (IMRT) based radiation plan or optimize a volumetric modulated arc therapy (VMAT) based radiation plan. For instance, the objective function can be defined to optimize an IMRT based radiation plan or to optimize a VMAT based radiation plan. In VMAT, a Multi Leaf Collimator (MLC) that is mounted on the head of the gantry is used to shape the radiation beam. The MLC includes a set of metal leaves that move in-and-out and block parts of the radiation to modulate the beam and make the radiation more conformal to the PTV shape. In VMAT, the gantry can deliver the radiation continuously while moving around the patient, while the MLC may block the radiation at some portions of the path. As such, the treatment path optimization in VMAT may involve determining segments of the path during which the MLC blocks the radiation. In IMRT, the gantry stops at few angles (e.g., about 5 to 10 angles) and delivers the radiation by modulating the beams. As such, the path optimization can include determining the (gantry angle, couch angle) pairs at which the gantry stops to deliver radiation to the patient.

One should note that the examples discussed in this specification are provided for illustrative purposes and re not to be interpreted as limiting. For example, the estimate of the radiation dose distribution can defined using other functions different from the function D(x) described in equation (1). Also, the computing system 150 can initiate the path search algorithm in various different ways.

Each method described in this disclosure can be carried out by computer code instructions stored on computer-readable medium. The computer code instructions, when executed by one or more processors of a computing device, can cause the computing device to perform that method.

While the disclosure has been particularly shown and described with reference to specific embodiments, it should be understood by those skilled in the art that various changes in form and detail may be made therein without departing from the spirit and scope of the invention described in this disclosure.

While this disclosure contains many specific embodiment details, these should not be construed as limitations on the scope of any inventions or of what may be claimed, but rather as descriptions of features specific to particular embodiments of particular inventions. Certain features described in this specification in the context of separate embodiments can also be implemented in combination in a single embodiment. Conversely, various features described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated in a single software product or packaged into multiple software products.

References to "or" may be construed as inclusive so that any terms described using "or" may indicate any of a single, more than one, and all of the described terms.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain embodiments, multitasking and parallel processing may be advantageous.

What is claimed is:

1. A method of radiation treatment planning comprising:
   determining, by one or more processors, an estimate of a radiation dose distribution within an anatomical region of a patient;
   determining, by the one or more processors, using the estimate of the radiation dose distribution, an objective function defined within the anatomical region of the patient in terms of the estimate of the radiation dose distribution and patient specific data;
   determining, by the one or more processors, for each radiation beam orientation of a plurality of radiation beam orientations, a corresponding conflict severity value using the objection function, the corresponding conflict severity value indicative of a severity of violating one or more clinical goals if the anatomical region of the patient is radiated according to each radiation beam orientation of the plurality of radiation beam orientations; and
   determining, by the one or more processors, using conflict severity values corresponding to the plurality of radiation beam orientations, a sequence of radiation beam orientations among the plurality of radiation beam orientations representing a treatment path.

2. The method of claim 1, wherein determining the estimate of the radiation dose distribution within the anatomical region of the patient includes determining the estimate of the radiation dose distribution as a function of a distance from a planning target volume (PTV) of the anatomical region of the patient.

3. The method of claim 1, wherein the objective function reflects one or more radiation constraints for the patient.

4. The method of claim 1, wherein the objective function is defined to optimize an intensity-modulated radiation therapy (IMRT) based radiation plan.

5. The method of claim 1, wherein the objective function is defined to optimize a volumetric-modulated arc therapy (VMAT) based radiation plan.

6. The method of claim 1, further comprising:
determining the plurality of radiation beam orientations by discretizing a space of possible radiation beam orientations, each point of the discretized space of possible radiation beam orientations represents a corresponding gantry-couch radiation beam orientation of the plurality of radiation beam orientations.

7. The method of claim 1, wherein determining, for each radiation beam orientation of the plurality of radiation beam orientations, the corresponding conflict severity value includes applying, for each radiation beam orientation, a weighting function to values of the objective function at voxels of the anatomical region of the patient.

8. The method of claim 7, wherein applying the weighting function includes weighting the values of the objective function at the voxels of the anatomical region of the patient according to a depth relative to a planning target volume (PTV) inside the anatomical region of the patient in a direction along each radiation beam orientation of the plurality of radiation beam orientations.

9. The method of claim 1, wherein determining the sequence of radiation beam orientations includes:
generating, by the one or more processors, a matrix of the conflict severity values corresponding to the plurality of radiation beam orientations among the plurality of radiation beam orientations; and
determining the sequence of radiation beam orientations among the plurality of radiation beam orientations using the matrix of the conflict severity values corresponding to the plurality of radiation beam orientations.

10. The method of claim 9, wherein determining the sequence of radiation beam orientations among the plurality of radiation beam orientations includes determining a sequence of conflict severity values within the matrix having a minimum total sum, each conflict severity value of the sequence of conflict severity values corresponding to a radiation beam orientation of the sequence of radiation beam-orientations among the plurality of radiation beam orientations.

11. A radiation treatment planning system comprising:
one or more processors; and
a non-transitory memory to store computer code instructions, the computer code instructions when executed cause the one or more processors to:
determine an estimate of a radiation dose distribution within an anatomical region of a patient;
determine, using the estimate of the radiation dose distribution, an objective function defined in terms of the estimate of the radiation dose distribution and patient specific data;
determine, for each radiation beam orientation of a plurality of radiation beam orientations, a corresponding conflict severity value using the objection function, the corresponding conflict severity value indicative of a severity of violating one or more clinical goals if the anatomical region of the patient is radiated according to each radiation beam orientation of the plurality of radiation beam orientations; and
determine, using conflict severity values corresponding to the plurality of radiation beam orientations, a sequence of radiation beam orientations among the plurality of radiation beam orientations representing a treatment path.

12. The radiation treatment planning system of claim 11, wherein in determining the estimate of radiation dose distribution within the anatomical region of the patient, the one or more processors are configured to determine the estimate of the radiation dose distribution as a function of a distance from a planning target volume (PTV) of the anatomical region of the patient.

13. The radiation treatment planning system of claim 11, wherein the objective function reflects one or more radiation constraints for the patient.

14. The radiation treatment planning system of claim 11, wherein the objective function is defined to optimize an intensity modulated radiation therapy (IMRT) based radiation plan or to optimize a volumetric-modulated arc therapy (VMAT) based radiation plan.

15. The radiation treatment planning system of claim 11, wherein the one or more processors are further configured to:
determine the plurality of radiation beam orientations by discretizing a space of possible radiation beam orientations, each point of the discretized space of possible radiation beam orientations represents a corresponding radiation beam orientation of the plurality of radiation beam orientations.

16. The radiation treatment planning system of claim 11, wherein in determining, for each radiation beam orientation of the plurality of radiation beam orientations, the corresponding conflict severity value, the one or more processors are configured to apply, for each radiation beam orientation, a weighting function to values of the objective function at voxels of the anatomical region of the patient.

17. The radiation treatment planning system of claim 16, wherein in applying the weighting function, the one or more processors are configured to weight the values of the objective function at the voxels of the anatomical region of the patient according to a depth relative to a planning target volume (PTV) inside the anatomical region of the patient in a direction along each radiation beam orientation of the plurality of radiation beam orientations.

18. The radiation treatment planning system of claim 11, wherein in determining the sequence of radiation beam orientations among the plurality of radiation beam orientations, the one or more processors are configured to:
generate a matrix of the conflict severity values corresponding to the plurality of radiation beam orientations; and
determine the sequence of radiation beam orientations among the plurality of radiation beam orientations using the matrix of the conflict severity values corresponding to the plurality of radiation beam orientations.

19. The radiation treatment planning system of claim 18, wherein in determining the sequence of radiation beam orientations among the plurality of radiation beam orientations, the one or more processors are configured to determine within the matrix a sequence of conflict severity values having a minimum total sum, each conflict severity value of the sequence of conflict severity values corresponding to a radiation beam orientation of the sequence of radiation beam orientations among the plurality of radiation beam orientations.

20. A non-transitory computer-readable medium including computer code instructions stored thereon, the computer code instructions when executed cause one or more processors to:
  determine an estimate of a radiation dose distribution within an anatomical region of a patient;
  determine, using the estimate of the radiation dose distribution, an objective function defined within the anatomical region of the patient in terms of the estimate of the radiation dose distribution and patient specific data;
  determine, for each radiation beam orientation of a plurality of radiation beam orientations, a corresponding conflict severity value using the objection function, the corresponding conflict severity value indicative of a severity of violating one or more clinical goals if the anatomical region of the patient is radiated according to each radiation beam orientation of the plurality of radiation beam orientations; and
  determine, using conflict severity values corresponding to the plurality of radiation beam orientations, a sequence of radiation beam orientations among the plurality of radiation beam orientations representing a treatment path.

* * * * *